United States Patent [19]

Pastrone et al.

[11] Patent Number: 4,821,558
[45] Date of Patent: Apr. 18, 1989

[54] ULTRASONIC DETECTOR

[75] Inventors: John Pastrone, Los Gatos; George H. Fellingham, San Jose; Michael Lawless, Boulder Creek, all of Calif.

[73] Assignee: Abbott Laboratories, North Chicago, Ill.

[21] Appl. No.: 45,951

[22] Filed: May 1, 1987

[51] Int. Cl.⁴ .............................................. G01N 7/00
[52] U.S. Cl. .......................................... 73/19; 73/61 R
[58] Field of Search ................. 73/19, 23, 24, 61 R; 128/DIG. 13; 604/123, 124

[56] References Cited

U.S. PATENT DOCUMENTS

| | | | |
|---|---|---|---|
| 3,648,694 | 3/1972 | Mogos et al. | 128/214 F |
| 3,898,637 | 8/1975 | Wolstenholme | 340/239 R |
| 3,908,441 | 9/1975 | Virloget | 73/55 |
| 4,014,206 | 3/1977 | Taylor | 73/19 |
| 4,112,773 | 9/1978 | Abts | 73/642 |
| 4,126,132 | 11/1978 | Portner et al. | 128/214 F |
| 4,333,016 | 6/1982 | Bilstad et al. | 250/577 |
| 4,341,116 | 7/1982 | Bilstad et al. | 73/290 V |
| 4,354,502 | 10/1982 | Colley et al. | 128/663 |
| 4,355,238 | 10/1982 | Ruell | 250/577 |
| 4,418,565 | 12/1983 | St. John | 73/19 |
| 4,432,231 | 2/1984 | Napp et al. | 73/290 V |
| 4,487,601 | 12/1984 | Lindemann | 604/122 |
| 4,501,531 | 2/1985 | Bilstad et al. | 417/63 |
| 4,758,228 | 7/1988 | Williams | 604/153 |

Primary Examiner—Stewart J. Levy
Assistant Examiner—Louis M. Arana
Attorney, Agent, or Firm—Christensen, O'Connor, Johnson & Kindness

[57] ABSTRACT

An ultrasonic detector for detecting air in a fluid. A fluid pumping cassette includes an elastomeric member that defines three sides of a fluid passageway, a base of the cassette defining the other side. Resilient lobes on the elastomeric member extend outwardly in opposite directions on each side of the passageway, directly contacting an ultrasonic sound generator on one side and a piezoelectric sound receiver on the opposite side, the direct contact enhancing transmission of an ultrasound signal through the elastomeric member to facilitate detection of an air bubble in the fluid passage.

4 Claims, 5 Drawing Sheets

ULTRASONIC DETECTOR

BACKGROUND OF THE INVENTION

The present invention relates to a detector which is adapted to detect whether a gas or a liquid is present in a fluid delivery conduit. The detector of the present invention is particularly suited for use as a low cost air-in-line detector in intravenous flow control equipment for delivering intravenous fluid to patients.

In administering intravenous fluid to patients, it is important to monitor the fluid being administered for the presence of air because if air is infused into a patient, an embolism can occur. Air can be introduced into a system through a leak in a tubing connector, through a crack in the equipment, or when the container from which the fluid is delivered is emptied. In some cases, particularly with flexible walled IV containers, the container is not completely filled at the factory, leaving an air space. This air may be infused into the patient if the fluid is delivered with a volumetric pump.

However, optical detectors can often produce false air-in-line signals when the tube or conduit is actually filled with liquid. Some IV fluids scatter and do not focus light, particularly IV fluids which contain particulates. Some IV fluids may be semi-opaque. The result is that the detector cannot distinguish between a liquid filled and an air filled conduit.

Furthermore, optical detectors of the type described above require the use of clear plastics in the liquid conduit. However, many useful medical grade plastics are not clear, so an optical detector cannot be used with them.

SUMMARY OF THE INVENTION

The present invention is an ultrasonic liquid detector comprising an ultrasonic sound generator and an ultrasonic sound receiver spacedly disposed from one another so as to receive a liquid carrying member therebetween. The sound generator and receiver each include a substrate and a layer of conductive material in the substrate. The conductive layer has at least two regions electrically isolated from each other. A piezoelectric chip is placed in electrical contact over at least a portion of the first region of the conductive layer. A conductive member extends between the piezoelectric chip and the second region of the conductive layer. An electrical signal having a frequency at the resonant frequency of the piezoelectric chip on the sound generator can be applied between the first and second regions of the sound generator conductive layer to cause ultrasonic sound to be generated. Ultrasonic sound can be received by the piezoelectric chip on the sound receiver and can be electrically detected by monitoring the electric signal produced between the first and second regions of the conductive layer on the sound receiver.

Other aspects of the present invention include an air-in-line detection assembly including an elastomeric member with a fluid passage therethrough and having a pair of resilient lobes extending in opposite direction therefrom and having a fluid passageway therethrough. An ultrasonic sound generator and an ultrasonic sound receiver are spacedly positioned from and facing each other. The elastomeric member is positioned between the sound generator and receiver and the sound generator and receiver are spaced such that the lobes are compressed inwardly of the elastomeric member so that each lobe maintains close contact with one of the sound generator and receiver. The present invention provides an ultrasonic detector which is reliable, easy to manufacture, and allows the member, through which fluid flows, to be readily engaged with and/or disengaged from the ultrasonic detector. These and other advantages of the present invention will become apparent from the disclosure which follows.

DETAILED DESCRIPTION OF THE PREFERRED EMBODIMENT

Figure 3:
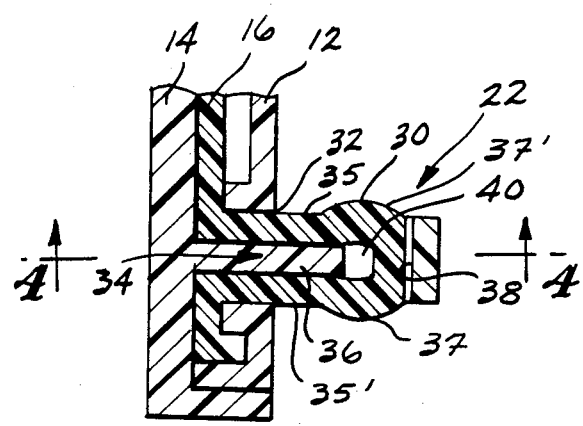
FIG. 3 is a cross section taken along the plane of line III—III of FIG. 1.
Figure 4:
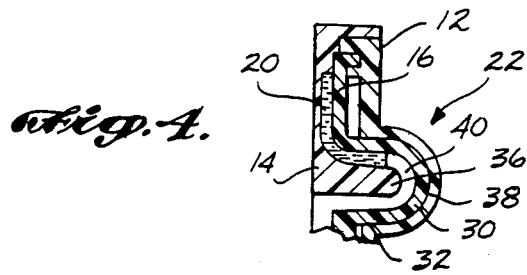
FIG. 4 is a cross section taken along the plane of line IV—IV FIG. 3.

The present invention is an ultrasonic air-in-line detector system particularly adapted for use with a disposable intravenous fluid pumping cassette disclosed in U.S. patent application Ser. No. 045,959 entitled Disposable Fluid Infusion Pumping Chamber Cassette, filed by Giovanni Pastrone on an even date herewith, the disclosure of which is incorporated herein by reference. The pumping cassette 10 includes a rigid face member 12 and a rigid back member 14 with elastomeric member 16 positioned therebetween (FIGS. 3-4). The cassette includes an inlet 18 to receive fluid from a fluid source (not shown) and an outlet (not shown) for delivering fluid at a positive pressure to the patient. Between the inlet and outlet is a fluid path 20 (FIG. 4) through air-in-line detection means 22, 24 which project outwardly from the surface of face member 12. Air-in-line detection means 22 engages an ultrasonic detector 26. Air-in-line detection means 24 engages ultrasonic detector 28. Air-in-line detection means 22 is identical to air-in-line detection means 24, so only one of them will be described in detail. Likewise, ultrasonic detector 26 is structurally the same as ultrasonic detector 28, so only the former will be described. Basically, the fluid path through the cassette passes through both air-in-line detection means 22 and 24, and ultrasonic detectors 26 and 28 are adapted to detect the presence of air being pumped through pumping cassette 10 to prevent air from being pumped into the patient.

Figure 1:
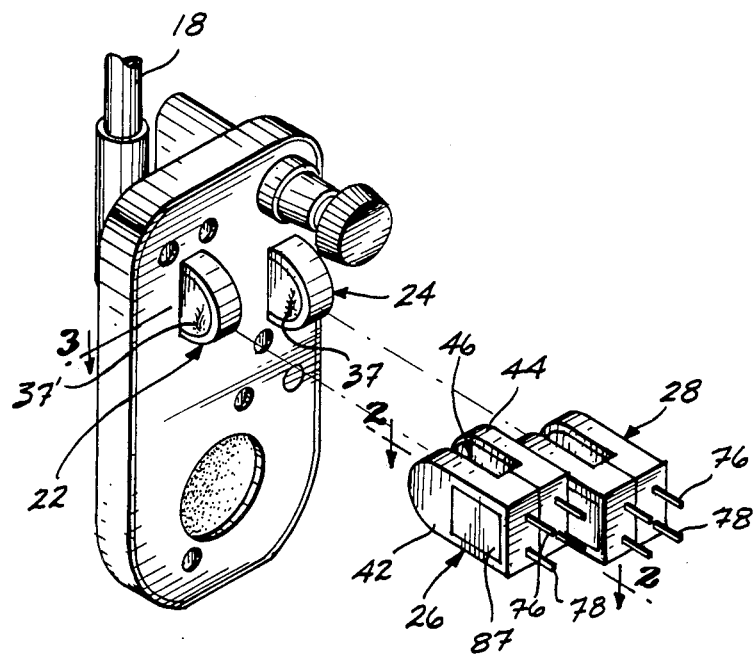
FIG. 1 is a perspective view of a disposable pump cassette featuring one aspect of the present invention together with ultrasonic detectors of the present invention.
Figure 3A:
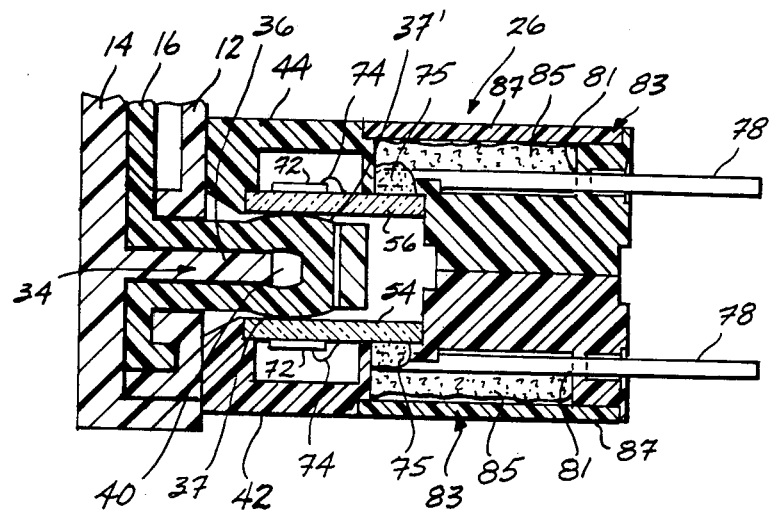
FIG. 3A is a cross-sectional view of the components of FIGS. 2 and 3 shown in engaged position.

Air-in-line detection means 22 includes a pocket 30 formed integrally as part of elastomeric member 16. Pocket 30 extends through an opening 32 in face member 12 and projects outwardly beyond the surface of face member 12. (FIGS. 1, 3, 3A. and 4). Pocket 30 has a hollow recess 34 within it which is formed within two sidewalls 35 and 35' and an arcuate endwall 38. A finger 36 projects from the inner surface of back member 14 into recess 34 and fits interferingly between sidewalls 35 and 35', but does not contact endwall 38. Rather, a fluid passage 40 is formed between the inside surfaces of endwall 38 and the perimeter of finger 36 which forms part of the fluid path 20 through the cassette. Fluid passage 40 allows the fluid flowing through fluid path 20 in the cassette to loop outwardly from the surface of face member 12 so that any air in the fluid path can be detected by an ultrasonic detector 26 (or 28) outside of the cassette. Ultrasonic detectors 26 and 28 are to be mounted on a cassette driver, a nondisposable item, whereas the cassette is inexpensive and disposable after each use.

Ultrasonic detector 26 includes two substantially mirror image housing portions 42 and 44. Housing member 42 is generally L-shaped and is joined to the mirror image L-shaped housing 44 at the bottom of the L's so as to form a U-shaped housing assembly with recess 46 between the arms of the U adapted to receive air-in-line detection means 22. On one side of recess 46, housing portion 42 has an opening 48, while on the other side of recess 46, housing portion 44 has an opening 50. Housing members 42 and 44 are hollow, each containing a passage 52 for the necessary electrical pins described below. Positioned across opening 48 is an ultrasonic generator 54, facing an ultrasonic receiver 56 positioned in opening 50 across recess 46. Ultrasonic generator 54 is structurally the same as ultrasonic receiver 56, so only ultrasonic generator 54 will be described.

Ultrasonic generator 54 (FIG. 5-7) includes a substrate 58, preferably made of glass coated on one side with a conductive layer 60, preferably on a layer of gold. Conductive layer 60 includes three sections 62, 64, and 66 which are electrically isolated from one another with a gap 68 between regions 62 and 64 and between regions 64 and 66, and a gap 70 which divides regions 60 and 62. A chip 72 made of a piezoelectric material such as lead zirconate titanate (PZT), preferably a Murata P7 or Valpey-Fisher PZT-5H piezoelectric crystal, is adhered to conductive layer 60 with a conductive epoxy adhesive, and is positioned such that one face of chip 72 overlays at least a portion of layer region 64, but the same face does not contact layer region 66. A conductive filament 74 extends from the opposite face of chip 72 to layer region 66, establishing an electrical connection therebetween.

Figure 2:
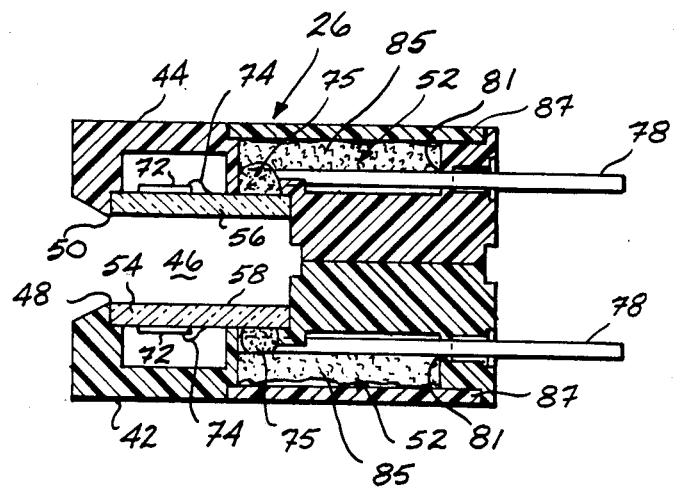
FIG. 2 is a cross section of one of the ultrasonic detectors of FIG. 1 taken along the plane of line II—II of FIG. 1.
Figure 5:
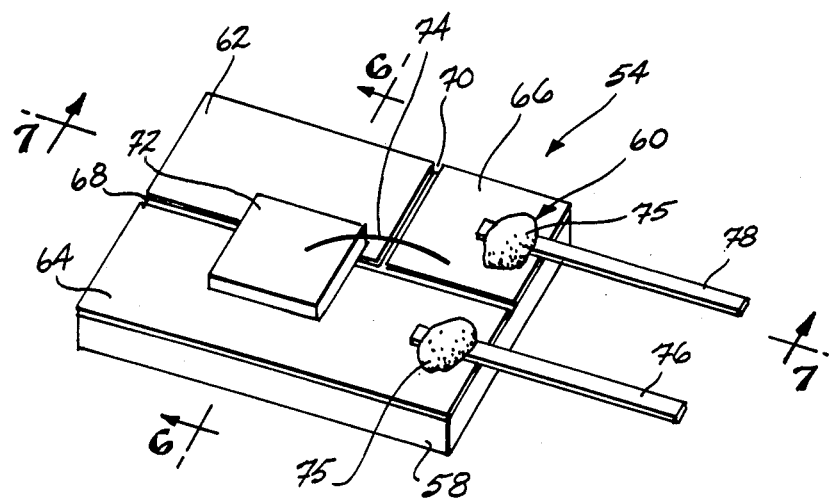
FIG. 5 is a perspective view of the ultrasonic sound generator and/or the ultrasonic sound receiver employed in the ultrasonic detector of FIG. 2.
Figure 6:
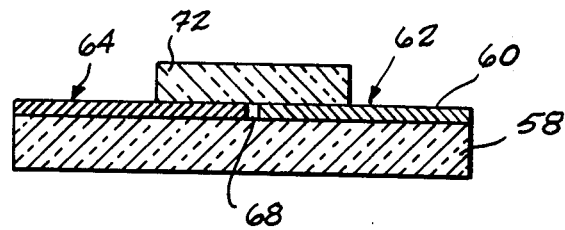
FIG. 6 is a cross section taken along the plane of lines VI—VI of FIG. 5.
Figure 7:
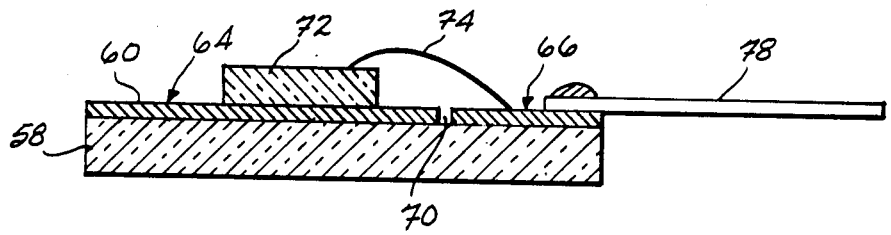
FIG. 7 is a cross section taken along the plane of line VII—VII of FIG. 5.

An electrically conductive pin 76 is electrically connected to layer region 64 while a pin 78 is electrically connected to layer region 66. This electrical connection is accomplished by glueing each pin to the appropriate region with an electrically conductive epoxy adhesive 75 (FIGS. 2, 3A and 5). When the assembly shown in FIGS. 5-7 is used as an ultrasonic generator, an electrical signal having a frequency the same as the resonant frequency of piezoelectric chip 72 is applied to chip 72 across leads 76 and 78 with the circuitry described below to conductive regions 60 and 64 through filament 74, to excite the chip to emit a high frequency sound. As shown in FIGS. 1, 2 and 3A, pins 76 and 78 extend out of housings 42 and 44. Housings 42 and 44 are mounted on a printed circuit board (not shown) through which pins 76 and 78 extend to connect to the circuitry described below.

To assemble an ultrasonic generator or receiver, chip 72 is mounted on substrate 58 by conductive adhesive. Filament 74 is attached as described above. Substrate 58 is then positioned in the opening 48 (or 50). Pin 78 (or 76) is inserted through a narrow aperture 81 (FIG. 2) in the rear of housing 42 (or 44) until the proximal end of the pin is positioned over the appropriate conductive region on the substrate. Through a large opening 83 (FIGS. 2 and 3A) in the side of housing 42 (or 44), conductive adhesive 75 is applied to adhere the proximal end of each pin 78 (and 76) to the appropriate conductive region on the substrate. These pins 76 and 78 are "potted" within housings 42 and 44 by filling the housings with non-conductive epoxy adhesive 85 (FIGS. 2 and 3A). Thus, openings 81 and adhesive 85 hold pins 76 and 78 immovably within housings 42 and 44 so they cannot be dislodged from electrical contact with substrates 56 and 58.

Openings 83 in housings 42 and 44 are covered by covers 87 (FIG. 1) before adhesive 85 sets. Ultrasonic detectors 26 and 28 are then mounted on a printed circuit board (not shown) through which pins 76 and 78 extend. The distal ends of pins 76 and 78 are then soldered to make electrical connection with the circuitry described below on the printed circuit board. To function as an ultrasonic receiver 56, the assembly shown in FIGS. 5-7 receives the ultrasonic sound generated by ultrasonic generator 54. The ultrasonic vibration is picked up by chip 72' and is converted to an electrical signal which is transmitted across filament 74 and through layers 60 and 64 to pins 76 and 78 (FIG. 1) where the high frequency electrical signal can be converted and amplified by the circuitry described below into a usable signal to sound an alarm in the event that air is present is fluid passage 40.

Elastomeric pocket 30 has two resilient lobes 37, 37' (FIGS. 1 and 3) which extend outwardly from sidewalls 35. The width of pocket 30 between lobes 37, 37' is somewhat less than the width of recess 46 between ultrasonic generator 54 and ultrasonic receiver 56 so that lobes 37 and 37' are compressed inwardly toward each other when air-in-line detection means 22 is inserted into ultrasonic detector 26 as shown in FIG. 3A. This insures that there will be good acoustic contact between ultrasonic generator 54 and pocket 30 and between ultrasonic receiver 56 and pocket 30.

This arrangement also allows the air-in-line detection means 22 to be inserted and withdrawn easily from recess 46. As shown in FIG. 3A, chips 72 and 72' align with fluid passage 40 so that an ultrasonic signal is transmitted across fluid passage 40 when air-in-line detection means 22 is inserted into recess 46. The transmission of ultrasonic sound between ultrasonic generator 54 and ultrasonic receiver 56 is greatly enhanced when a liquid is present in passage 40. But when air is present in passage 40, the transmission of ultrasonic sound through fluid passage 40 is attenuated. This difference in ultrasonic sound transmission is detected by ultrasonic receiver 56. When air is present, the signal from ultrasonic receiver 56 drops. When a signal drops, an alarm (not shown) is sounded to stop the pumping of fluid through the cassette if the cassette is in the fluid delivery cycle.

As disclosed in co-pending application, Ser. No. 045,959, entitled Disposable Fluid Infusion Pumping Chamber Cassette, filed by Giovanni Pastrone on an even date herewith, the ultrasonic detectors and air-inline detectors disclosed herein can be used also to check the integrity of several of the cassette components when the cassette is not in the fluid delivery part of its pumping cycle.

As indicated above, ultrasonic detectors 26 and 28 are parts of a nondisposable cassette driver, and cassette 10 is a disposable item. As cassette 10 is mounted on the driver, air-in-line detection means 22 and 24 slide easily into recesses 46 in ultrasonic detectors 26 and 28, but nonetheless intimate sound transmitting contact is achieved between each air-in-line detection means and its associated detector through diodes 37 and 37'. Lobes 37, 37' deflect inwardly as an air-in-line detector is slid into a recess 46, creating the desired contact, but the lobes do not interfere with the sliding insertion of the air-in-line detectors into the ultrasonic detectors.

Figure 8:
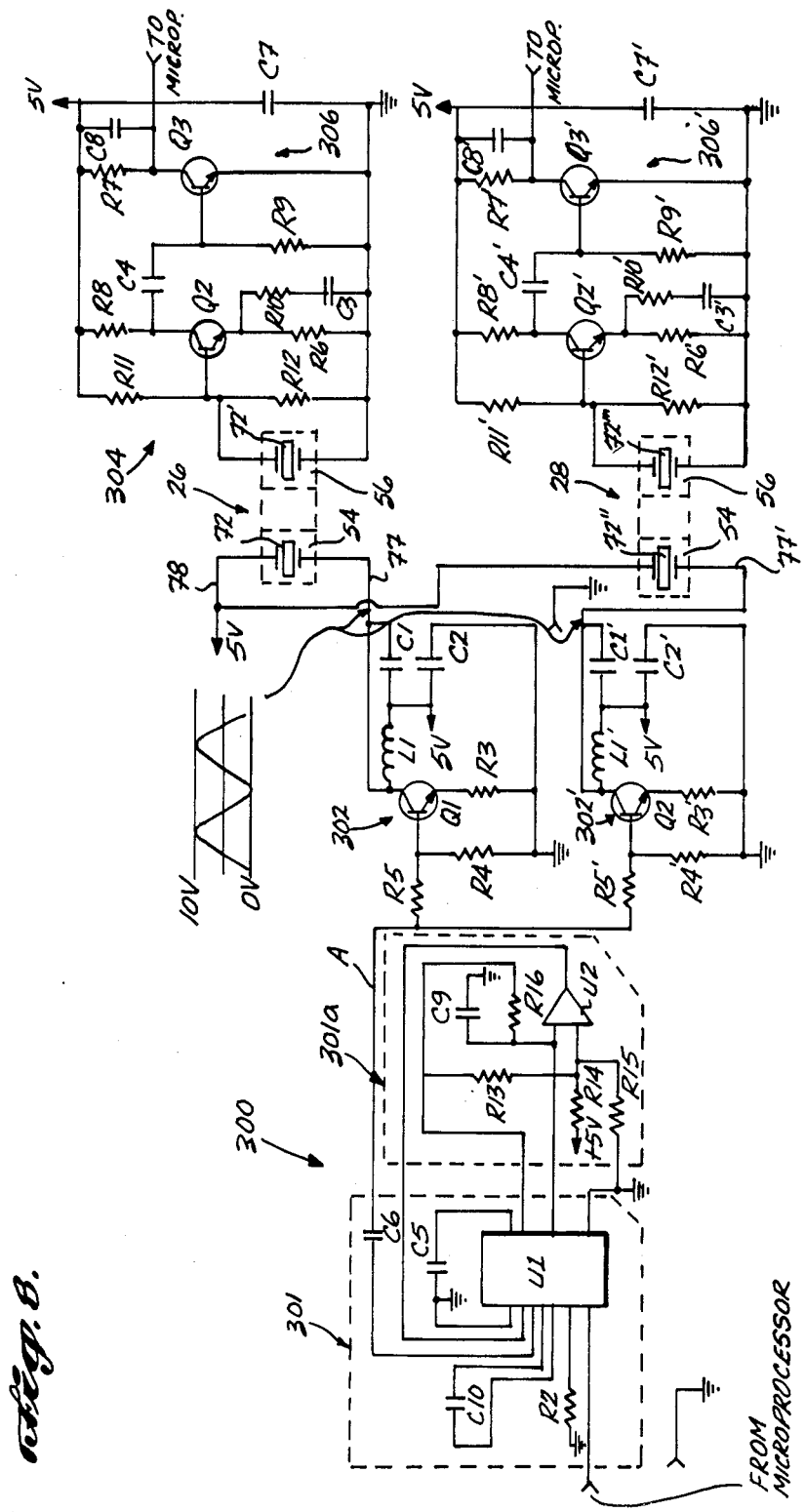
FIG. 8 is a schematic of the circuitry used in the air-in-line detection system of the present invention.

The circuitry for the air-in-line detection system for the cassette driver of the present invention is illustrated in FIG. 8. The transmitting crystals 72 and 72" of ultrasonic detectors 26 and 28, respectively are controlled by a pair of amplifier circuits 302 and 302'. Amplifier circuits 302 and 302' are driven, in turn, by a sweep oscillator 300 which includes a voltage controlled oscillator 301 and a triangle wave oscillator 301a.

Each crystal (72—72''') will resonate at a variety of frequencies, but each has several peak resonating frequencies including one having a nominal value of about 5.00 MHz. However, the resonant frequency of a given crystal can vary from the nominal values. Furthermore, the resonant frequency of a crystal can shift when it is mounted on a substrate 58. To reduce the difference between the resonant frequencies of transmitting and receiving crystals, each pair of such crystals should be cut from the same piece of piezoelectric material. Furthermore, each pair should be mounted on substrates cut from the same larger piece of material. Such precautions sufficiently reduce the frequency differences between transmitting and receiving crystals, which with imperfectly matched crystals could otherwise lead to a false alarm that air is in the cassette.

Figure 9:
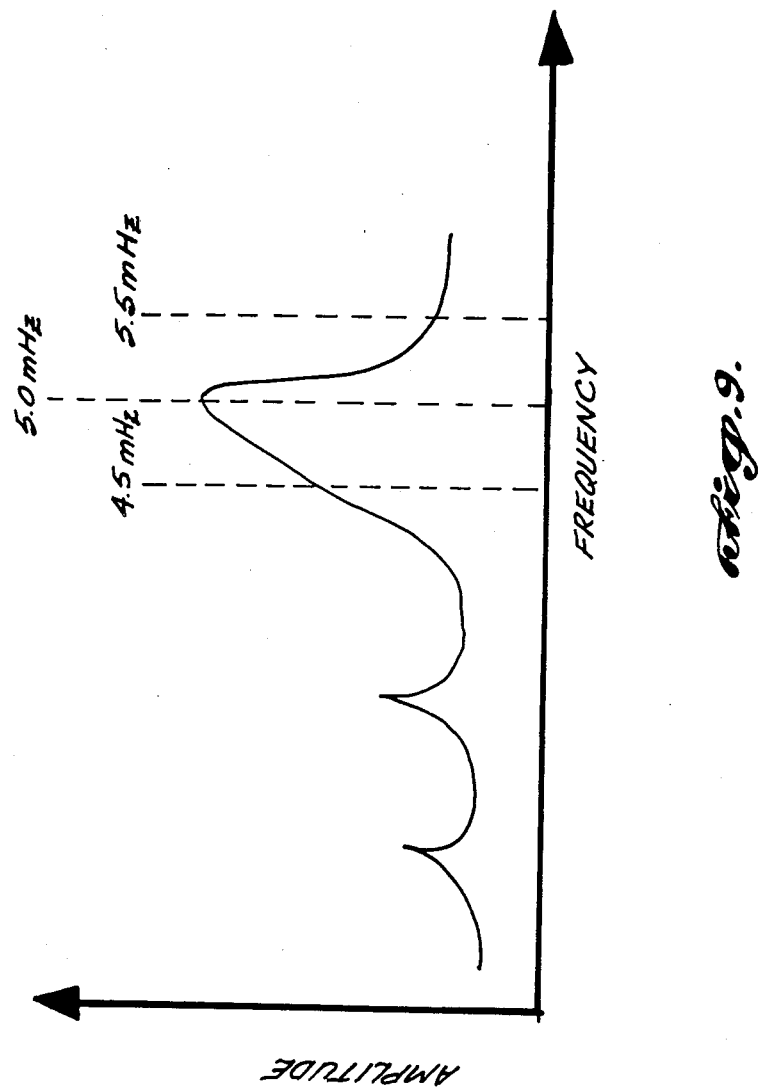
FIG. 9 is a graph of the frequency response of a piezoelectric chip.

However, a problem arises in that the resonant frequency of each pair of transmitting and receiving crystals can vary from pair to pair. FIG. 9 shows the frequency response of a given crystal having a 5 MHz peak resonating frequency as well as several lower resonating frequencies. As shown in FIG. 9, for example, the pairs are selected from materials which have nominal peak frequencies of about 5 MHz, but the peak frequencies can vary as much as ±10 percent (i.e., 4.50-5.50 MHz), thus, the circuitry to resonate the crystals must be capable of resonating any selected pair within this range if one wishes to avoid having to calibrate each circuit to each pair of crystals. This individual calibration would be extremely laborious.

Sweep oscillator 300 varies the frequency of the electrical signal applied to the the transmitting crystals (72 and 72") over this relatively broad frequency spectrum (i.e., 5 MHz ±10%). It has been observed that this spectrum includes the resonant frequencies of the pairs of crystals which will be installed in the cassette driver. In other words, sweep oscillator 300 will hit a frequency for each pair of crystals which produces a sufficient response to avoid false signals. However, if the frequency of the electrical signal applied to the matched pair of crystals is varied across the range between 4.50 and 5.50 MHz (i.e., a range is swept), there will be an intermediate frequency within the range where the transmitting chip will emit acoustic signals having an amplitude sufficient to excite the receiving crystal. This avoids the false alarm situation where the transmitting crystals is resonated at a frequency which is sufficiently different from its natural peak resonant frequency to "fool" the system that air is in the cassette.

Voltage controlled oscillator (VCO) 301 consists of a 74HC4046 phase locked loop oscillator U1 with only the voltage controlled oscillator section being used. VCO 301 output is coupled by capacitor $C_6$ to the transmitting crystal drivers $Q_1$ and $Q_2$.

VCO 301 is driven by triangle wave oscillator (TW Oscillator) 301a formed by an amplifier U2 with capacitor $C_9$ and resistors $R_{13}$-$R_{16}$. TW Oscillator 301a uses an exclusive OR gate inside VCO 301 as a voltage buffer which improves the symmetry of its output waveform.

TW Oscillator 301a has a frequency of about 3 kHz and a peak-to-peak amplitude of about 1.0 volt with an average value of 2.5 volts. This causes VCO 301 to sweep over a 2 MHz range, covering the required 4.50 to 5.50 MHz range plus to allow component tolerances in the oscillator.

The "timing elements" of VCO 301, namely resistor $R_2$ and capacitor $C_{10}$ are seleced so that the sweep range of VCO 301 includes frequencies at which the ceramic material used for the transmitting and receiving crystals will resonate.

Line A from VCO 301 is bifurcated into lines B and C, each of which applies the signals generated by VCO 301 to an amplifier circuit 302 or 302', each of which is identical to the other. Each amplifier circuit 302 or 302' (described in detail below) amplifies the signal to identical 10 volt peak to peak sine wave voltage signals at lines 76 and 76', respectively. The frequency of the signal at lines 77 and 77' will vary within the range of sweep oscillator 300.

Amplifier circuit 302 includes a transistor $Q_1$. Transistor $Q_1$ together with resistors $R_3$, $R_4$ and $R_5$, capacitors $C_1$ and $C_2$, and coil $L_1$ form a Class C amplifier. Thus, $L_1$, $C_1$ and the crystal 72 form a tuned load, nominally resonant at 5 MHz. However, the actual resonance of this tuned load varies for reasons explained above. Crystal 72 is a Valpey-Fisher PZT-5H or a Murata P7 piezoelectric crystal.

The amplifier circuit 302' is identical to circuit 302 with $Q_1'$, $R_3'$, $R_4'$ etc. corresponding to $Q_1$, $R_3$, $R_4$ etc. Amplifier circuit 302 applies a high, variable frequency sine wave signal through line 77 to one side of piezoelectric crystal 72 of ultrasonic generator 54 of air-in-line detector 26. The other side of crystal 72 of ultrasonic generator 54 is connected to a 5 volt power supply (not shown) by line 78. The 5 MHz signal applied across crystal 72 excites crystal 72 to generate a high, variable frequency ultrasonic signal across the gap between ultrasonic generator 54 and the ultrasonic receiver 56.

As previously indicated, when there is water in the fluid path in air-in-line detector 26, the ultrasonic signal generated is received virtually unattenuated by ultrasonic receiver 56. However, the high frequency sound generated by ultrasonic generator 54 is greatly attenuated if air is present in air-in-line detector 56.

Transistor $Q_2$ and resistors $R_{12}$, $R_{11}$, $R_{10}$, $R_6$, and $R_8$, and capacitor $C_3$ form an AC coupled common emitter amplifier 304. Amplifier 304 is coupled to crystal 72' of receiver 54. Capacitor $C_4$ is an output coupling capacitor which is coupled to transistor $Q_3$. Transistor $Q_3$ forms a threshold voltage detector 306 with resistor $R_7$ and capacitor $C_8$.

When water is in air-in-line detector 26 crystal 72' is excited by one or more of the acoustic frequencies generated by crystal 72. The voltage signal received from amplifier 304 at the base of $Q_3$ is a sine wave having a 100 to 200 m V peak. Amplifier $Q_3$ increases that voltage to a sufficient level to cross the threshold formed by the base-emitter forward voltage at $Q_3$. Thus, the output voltage at $Q_3$ collector indicates the presence of water.

When air is in air-in-line detector 26, crystal 72' will not be excited by any of the frequencies generated by crystal 72. The signal received at the base of $Q_3$ falls below that necessary to cross the base-emitter threshold of $Q_1$. The output voltage at $Q_3$ collector indicates the presence of air. $Q_3$ collector is coupled to the microprocessor which detects the difference in voltage between the water/air situations. If air is in the sensor, the microprocessor sounds an alarm.

In practice, sweep oscillator 300 sweeps a range of electrical signal frequencies from about 4.50 MHz to about 5.50 MHz. The signal is amplified by amplifier 302, and the variable frequency signal is applied to the transmitting crystals. One or more of these frequencies will excite the transmitting crystals. If water is in the cassette, one or more of the high, variable frequency signals generated by the transmitting crystals will be received by and excite the receiving crystals. The signals generated by the receiving crystals will be amplified and indicate to the microprocessor that water is in the cassette. If air is in either of the air-in-line detection means 22 or 24, none of the acoustic frequencies emitted by transmitting crystals 72 or 72" will be sufficient to excite either of the receiving crystal 72' or 72''' adjacent the empty detection means 22 or 24. Thus, the microprocessor will sound an alarm.

While one embodiment of the invention has been disclosed, other embodiments will be apparent to those of ordinary skill in the art. These embodiments are to be included in the scope of the present invention unless the claims which follow expressly state otherwise.

I claim:

1. An air-in-line detector assembly, comprising:
   a supporting structure for the air-in-line detector;
   an elastomeric member that cooperates with the supporting structure to define a fluid passageway, said elastomeric member having a pair of resilient lobes extending in opposite directions about the fluid passageway;
   an ultrasonic sound generator comprising a first transducer, said first transducer being disposed in contact with one lobe of the elastomeric member and
   an ultrasonic sound receiver comprising a second transducer, said second transducer being disposed in contact with the other lobe of the elastomeric member, spacedly positioned apart from and facing said sound generator,
   said elastomeric member being positioned between said sound generator and receiver, and said sound generator and receiver being so spaced such that said lobes are compressed inwardly of said elastomeric member to insure that each lobe maintains close direct contact with one of said first and second transducers.

2. An apparatus for detecting air in a fluid pumping cassette having a fluid inlet, a fluid outlet, and a rigid housing formed of two housing portions with an elastomeric sheet sealed therebetween, comprising:
   a portion of said elastomeric sheet extending through an opening in one of said housing portions, and together with the housing portions, defining a fluid passage, one end of said fluid passage being in fluid communication with said fluid inlet, the other end of said fluid passage being in communication with said fluid outlet; and
   a source of oscillating energy, and a receiver of oscillating energy spaced apart from said energy source, said elastomeric sheet portion being disposed between said energy source and receiver and in contact with both, so that a liquid within the fluid passage provides more efficient coupling of the oscillating energy from the source to the receiver than does air.

3. The apparatus as recited in claim 2 wherein said energy source is an ultrasonic generator and said energy receiver is an ultrasonic receiver.

4. The apparatus as recited in claim 3 wherein said elastomeric sheet portion includes a pair of lobes extending in opposite directions so as to contact said source and receiver intimately.

* * * * *